(12) United States Patent
De Boer et al.

(10) Patent No.: US 10,321,652 B2
(45) Date of Patent: Jun. 18, 2019

(54) STAY GREEN CUCUMBER PLANT

(71) Applicant: Enza Zaden Beheer B.V., Enkhuizen (NL)

(72) Inventors: Geert Johannes De Boer, IJmuiden (NL); Mattheus Nicolaas Groot, Aguadulce (ES); Jeanine Danielle Louwerse, Amsterdam (NL); Wilhelmina Antonia Cornelia Anna Leijten, Vleuten (NL)

(73) Assignee: Enza Zaden Beheer B.V., Enkhuizen (NL)

( * ) Notice: Subject to any disclaimer, the term of this patent is extended or adjusted under 35 U.S.C. 154(b) by 9 days.

(21) Appl. No.: 15/328,682

(22) PCT Filed: Jul. 16, 2015

(86) PCT No.: PCT/EP2015/066310
§ 371 (c)(1),
(2) Date: Jan. 24, 2017

(87) PCT Pub. No.: WO2016/012346
PCT Pub. Date: Jan. 28, 2016

(65) Prior Publication Data
US 2017/0215361 A1    Aug. 3, 2017

(30) Foreign Application Priority Data

Jul. 25, 2014 (NL) ..................................... 2013260

(51) Int. Cl.
| | | |
|---|---|---|
| *A01H 5/08* | (2018.01) | |
| *C12N 15/82* | (2006.01) | |
| *C07K 14/415* | (2006.01) | |
| *A01H 6/34* | (2018.01) | |
| *A01H 1/04* | (2006.01) | |

(52) U.S. Cl.
CPC .............. *A01H 6/346* (2018.05); *A01H 1/04* (2013.01); *A01H 5/08* (2013.01); *C07K 14/415* (2013.01); *C12N 15/8251* (2013.01)

(58) Field of Classification Search
None
See application file for complete search history.

(56) References Cited

U.S. PATENT DOCUMENTS

| | | |
|---|---|---|
| 2012/0278944 A1 | 11/2012 | Wang et al. |
| 2015/0052636 A1* | 2/2015 | Hartig ................ C12N 15/8216 800/287 |

FOREIGN PATENT DOCUMENTS

| | | |
|---|---|---|
| EP | 1929039 B1 | 12/2009 |
| WO | 2007042070 A1 | 4/2007 |

OTHER PUBLICATIONS

Wyszogrodzka et al (1987, Plant Disease 71:275-280).*
Pan et al (2018, Theoretical and Applied Genetics 131:1577-1587), including 5 supplemental pages.*
Gen Bank AXF54554.1 (https://www.ncbi.nlm.nih.gov/protein/1433393282, accessed Aug. 28, 2018).*
Gen Bank MH493893.1 (https://www.ncbi.nlm.nih.gov/nuccore/1433393281, accessed Aug. 28, 2018).*
Henikoff et al.; "TILLING. Traditional Mutagenesis Meets Functional Genomics"; Plant Physiology; 2004; pp. 630-636; vol. 135.
McCallum et al.; "Targeted screening for induced mutations"; Nature Biotechnology; 2000; pp. 455-457; vol. 18.
Rong et al.; "The Stay-Green Rice like (SGRL) gene regulates chlorophyll degradation in rice"; Journal of Plant Physiology; 2013; pp. 1367-1373; vol. 170.
Till et al.; "Mismatch cleavage by single-strand specific nucleases"; Nucleic Acids Research; 2004; pp. 2632-2641; vol. 32:8.
Zhou et al.; "From Model to Crop: Functional Analysis of a Stay-Green Gene in the Model Legume *Medicago truncatula* and Effective Use of the Gene for Alfalfa Improvement"; Plant Physiology; 2011; pp. 1483-1496; vol. 157.

* cited by examiner

*Primary Examiner* — Anne Kubelik
(74) *Attorney, Agent, or Firm* — The Webb Law Firm (57) ABSTRACT

Provided herein is a Cucumber plant (*Cucumis sativus*) which provides fruits having an improved shelf life, wherein said plant comprises a stay green gene providing the improved fruit shelf life, wherein said stay green gene encodes a protein comprising the amino acid sequence as shown in SEQ ID No. 2, or amino acid sequences with more than 90% identity, preferably more than 94% identity, more preferably more than 96% identity, even more preferably more than 98% identity; and wherein the expression of said stay green gene is reduced as compared to the expression of said stay green gene in a cucumber plant not providing fruits having an improved shelf life or the enzymatic activity of said protein is reduced as compared to the enzymatic activity of said protein in a cucumber plant not providing fruits having an improved shelf life.

6 Claims, 8 Drawing Sheets

Specification includes a Sequence Listing.

SEQUENCE LISTING

<160> NUMBER OF SEQ ID NOS: 4

<210> SEQ ID NO 1
<211> LENGTH: 2501
<212> TYPE: DNA
<213> ORGANISM: Cucumis sativus

<400> SEQUENCE: 1

```
tgcttgtatt tttgggtcaa ataacagatt aatgtaaata aaattcgata tggaagtttg      60
aaagcattta gatagaatag catgtagtct aaaaatgtat ttagtggccg gtagagtata     120
caagtatttg tagtgggtag catccaaagt caaaaacaga gacggtgtcg tattattgat     180
caaccacgta aaatccccca aaggaaaaat aatggttgct tattacaacc aaacctaaac     240
gaagtctact acttgaagca acagcgaaga aaaagcaatt cctttcctac acgcttctaa     300
ttcccaaaaa ttctggactt cactactcat cagattatac acagcatttc cttttcatt      360 cttccccttt tctcttttt cttttttct tttgtttccc ataagcctca tattttgttc      420
ctccctaagt ttcctctgtt tttgatcctt taaaccgatc acaaaccctc ccaaatttct     480
ggagctaatt tgttggacaa gatgagggtt ttgactggta attcttctcc tcttcttgtt     540
ccttcttcaa accttatca cgattcttct tctctcttcc cctgtaaacg caaatccaag      600
aagaagaacc atggaatggt tcctgtaagt ttctttcttt ctttctttct tttttgggt      660 tttgttttgg ttttgatttt gattttgact ctgattttaa ttttatagat ggcgagattg     720
tttgggccag ccatatttga agcttcgaag ctaaaggttc tgttttagg ggtggatgag      780 aagaaacatc caggcaaatt tccaaggact tatacgctca cacatagtga tattacttct     840
aaacttactc ttgccatttc tcaatccatt aacaattctc aggtaactct tcttcttctt     900
cttcttttta gtttaatgaa aactcctttt ctagtttgtc aaatatttga aaattgatag     960
ttttgtttta gattataatt atgtgaaacg tgttttttat tcttgaataa tgcttctcat    1020
atcagatact tattgatttt tttcttcttt tccttttta tttagcttga agacacttct    1080
tcaatatttt ttaaaataaa atttaccaat atttagaaaa aaagaaaac aaagctatag     1140 ttttgaaaac ttaaaatag tttacaaac tatatcttct cggtattttg aatctgaatt     1200
ctattttaaa atttggttag aaattcaagt tttttaaga aaagtgaccg aatagagttt     1260
tgaagtccca acaatccaac tatatgggaa ctttatttc tggaatgggt gttaaataca     1320
ataaaaatgt aagtattgat gatgatggat gaatatatta ttacgcagtt acaaggatgg    1380
tataattggc ttcaaaggga tgaagtggta ggagaatgga agaaagttaa gggaaaaatg    1440
tctcttcatg ttcattgtca tatcagtggt ggccattttc ttctagatct ttgtgctaat    1500
ctcagatact tcatctttcg caaagaactc cctgtggtaa tttctctttc tcttcatcta    1560
ttatttacta taagatgcac aaaaactaca ggataaagaa tagactccaa tcattgatct    1620
atgagaagtt agatataaat tttacactat cagcaaatta cttgcatttg gatcatttga    1680
tgtctgctat ttttcattta cttgtccaat aaaaaaatta taatacatac cccacttctg    1740
aataatttat tatataattg acatttgatt cacacgatat aaaggtgttg aatgctttcg    1800
tccatggaga tgtggattta ttcaacaatt accctgaatt acaagaggct atggtttggg    1860
tttatttcca ctccaaaatt ccagaattca acaaggtaga gtgttgggc ccactgaagg     1920 atccagcccc accttcaact gggcttgatg ggtccactca aagccagccc atgtgggaat    1980
tgggcttgct ggagcggccc aaaccttgtc aagaagattg cacttgttgc ttcccaacca    2040
tcccttccat ttcatggtct cccaagaata atgagttgga gagcacatag attcatttta    2100
```

```
ttgactgccc ttaaaatgta aatagttcat ctttattgtt actatataat gacaattgaa    2160
tgttttcaac tttctattta gtccttatat ttcaattcgt taatctttgt agtatctaag    2220
atgttaaatt atatatcgtg gaaattttct tctttcaata gtgttttga tgaaatataa     2280 ggaaatttct cgttatgttt cgatgaaatc tttttttctag ttttaattat atcatgaatt   2340
tgtaataacc gagctaagat tgtagaaaaa caagttagac agttgtatgt tgcagacttg    2400
tgaattcctg catgctttgg agggattggt aaaattcttt taaaaaggg aagaaatgc      2460 ttatatgcat aaggaagaat tgacacaata tgctaccagt a                        2501
```

<210> SEQ ID NO 2
<211> LENGTH: 256
<212> TYPE: PRT
<213> ORGANISM: Cucumis sativus

<400> SEQUENCE: 2

```
Met Arg Val Leu Thr Gly Asn Ser Ser Pro Leu Leu Val Pro Ser Ser
 1               5                  10                  15

Asn Pro Tyr His Asp Ser Ser Leu Phe Pro Cys Lys Arg Lys Ser
                20                  25                  30

Lys Lys Lys Asn His Gly Met Val Pro Met Ala Arg Leu Phe Gly Pro
            35                  40                  45

Ala Ile Phe Glu Ala Ser Lys Leu Lys Val Leu Phe Leu Gly Val Asp
     50                  55                  60

Glu Lys Lys His Pro Gly Lys Phe Pro Arg Thr Tyr Thr Leu Thr His
 65                  70                  75                  80

Ser Asp Ile Thr Ser Lys Leu Thr Leu Ala Ile Ser Gln Ser Ile Asn
                 85                  90                  95

Asn Ser Gln Leu Gln Gly Trp Tyr Asn Trp Leu Gln Arg Asp Glu Val
            100                 105                 110

Val Gly Glu Trp Lys Lys Val Lys Gly Lys Met Ser Leu His Val His
        115                 120                 125

Cys His Ile Ser Gly Gly His Phe Leu Leu Asp Leu Cys Ala Asn Leu
    130                 135                 140

Arg Tyr Phe Ile Phe Arg Lys Glu Leu Pro Val Val Leu Asn Ala Phe
145                 150                 155                 160

Val His Gly Asp Val Asp Leu Phe Asn Asn Tyr Pro Glu Leu Gln Glu
                165                 170                 175

Ala Met Val Trp Val Tyr Phe His Ser Lys Ile Pro Glu Phe Asn Lys
            180                 185                 190

Val Glu Cys Trp Gly Pro Leu Lys Asp Pro Ala Pro Ser Thr Gly
        195                 200                 205

Leu Asp Gly Ser Thr Gln Ser Gln Pro Met Trp Glu Leu Gly Leu Leu
    210                 215                 220

Glu Arg Pro Lys Pro Cys Gln Glu Asp Cys Thr Cys Phe Pro Thr
225                 230                 235                 240

Ile Pro Ser Ile Ser Trp Ser Pro Lys Asn Asn Glu Leu Glu Ser Thr
                245                 250                 255
```

<210> SEQ ID NO 3
<211> LENGTH: 2501
<212> TYPE: DNA
<213> ORGANISM: Cucumis sativus

<400> SEQUENCE: 3

```
tgcttgtatt tttgggtcaa ataacagatt aatgtaaata aaattcgata tggaagtttg    60
aaagcattta gatagaatag catgtagtct aaaaatgtat ttagtggccg gtagagtata   120
caagtatttg tagtgggtag catccaaagt caaaaacaga gacggtgtcg tattattgat   180
caaccacgta aaatccccca aaggaaaaat aatggttgct tattacaacc aaacctaaac   240
gaagtctact acttgaagca acagcgaaga aaaagcaatt cctttcctac acgcttctaa   300
ttcccaaaaa ttctggactt cactactcat cagattatac acagcatttc cttttttcatt  360 cttccccttt tctctttttt cttttttttct tttgtttccc ataagcctca tattttgttc   420
ctccctaagt ttcctctgtt tttgatcctt taaaccgatc acaaaccctc ccaaatttct   480
ggagctaatt tgttggacaa gatgagggtt ttgactggta attcttctcc tcttcttgtt   540
ccttcttcaa acccttatca cgattcttct tctctcttcc cctgtaaacg caaatccaag   600
aagaagaacc atggaatggt tcctgtaagt ttctttcttt ctttctttct tttttgggt    660 tttgttttgg ttttgatttt gattttgact ctgattttaa ttttatagat ggcgagattg   720
tttgggccag ccatatttga agcttcgaag ctaaaggttc tgttttagg ggtggatgag   780 aagaaacatc caggcaaatt tccaaggact tatacgctca cacatagtga tattacttct   840
aaacttactc ttgccatttc tcaatccatt aacaattctc aggtaactct tcttcttctt   900 cttctttta gtttaatgaa aactcctttt ctagtttgtc aaatatttga aaattgatag   960
ttttgtttta gattataatt atgtgaaacg tgttttttat tcttgaataa tgcttctcat  1020
atcagatact tattgatttt tttcttcttt tcctttttta tttagcttga agacacttct  1080 tcaatattt ttaaaataaa atttaccaat atttagaaaa aaaagaaaac aaagctatag  1140
ttttgaaaac ttaaaaatag tttacaaaac tatatcttct cggtattttg aatctgaatt  1200
ctattttaaa atttggttag aaattcaagt ttttttaaga aaagtgaccg aatagagttt  1260
tgaagtccca acaatccaac tatatgggaa ctttattttc tggaatgggt gttaaataca  1320
ataaaaatgt aagtattgat gatgatggat gaatatatta ttacgcagtt acaaggatgg  1380
tataattggc ttcaaaggga tgaagtggta ggagaatgga agaaagttaa gggaaaaatg  1440
tctcttcatg ttcattgtca tatcagtggt ggccatttc ttctagatct ttgtgctaat   1500
ctcagatact tcatctttcg caaagaattc cctgtggtaa tttctctttc tcttcatcta  1560
ttatttacta taagatgcac aaaaactaca ggataaagaa tagactccaa tcattgatct  1620
atgagaagtt agatataaat tttacactat cagcaaatta cttgcatttg gatcatttga  1680
tgtctgctat ttttcattta cttgtccaat aaaaaaatta taatacatac cccacttctg  1740
aataatttat tatataattg acatttgatt cacacgatat aaaggtgttg aatgctttcg  1800
tccatggaga tgtggattta ttcaacaatt accctgaatt acaagaggct atggtttggg  1860
tttatttcca ctccaaaatt ccagaattca acaaggtaga gtgttggggc ccactgaagg  1920
atccagcccc accttcaact gggcttgatg ggtccactca aagccagccc atgtgggaat  1980
tgggcttgct ggagcggccc aaaccttgtc aagaagattg cacttgttgc ttcccaacca  2040
tcccttccat ttcatggtct cccaagaata atgagttgga gagcacatag attcattta   2100 ttgactgccc ttaaaatgta aatagttcat ctttattgtt actatataat gacaattgaa  2160
tgttttcaac tttctatttta gtccttatat ttcaattcgt taatctttgt agtatctaag  2220
atgttaaatt atatatcgtg gaaatttct tctttcaata gtgttttga tgaaatataa   2280 ggaaatttct cgttatgttt cgatgaaatc tttttctag ttttaattat atcatgaatt   2340
tgtaataacc gagctaagat tgtagaaaaa caagttagac agttgtatgt tgcagacttg  2400
```

```
tgaattcctg catgctttgg agggattggt aaaattcttt taaaaaaggg aagaaatgc    2460 ttatatgcat aaggaagaat tgacacaata tgctaccagt a                       2501

<210> SEQ ID NO 4
<211> LENGTH: 256
<212> TYPE: PRT
<213> ORGANISM: Cucumis sativus

<400> SEQUENCE: 4

Met Arg Val Leu Thr Gly Asn Ser Ser Pro Leu Leu Val Pro Ser Ser
1               5                   10                  15

Asn Pro Tyr His Asp Ser Ser Ser Leu Phe Pro Cys Lys Arg Lys Ser
            20                  25                  30

Lys Lys Lys Asn His Gly Met Val Pro Met Ala Arg Leu Phe Gly Pro
        35                  40                  45

Ala Ile Phe Glu Ala Ser Lys Leu Lys Val Leu Phe Leu Gly Val Asp
    50                  55                  60

Glu Lys Lys His Pro Gly Lys Phe Pro Arg Thr Tyr Thr Leu Thr His
65                  70                  75                  80

Ser Asp Ile Thr Ser Lys Leu Thr Leu Ala Ile Ser Gln Ser Ile Asn
                85                  90                  95

Asn Ser Gln Leu Gln Gly Trp Tyr Asn Trp Leu Gln Arg Asp Glu Val
            100                 105                 110

Val Gly Glu Trp Lys Lys Val Lys Gly Lys Met Ser Leu His Val His
        115                 120                 125

Cys His Ile Ser Gly Gly His Phe Leu Leu Asp Leu Cys Ala Asn Leu
    130                 135                 140

Arg Tyr Phe Ile Phe Arg Lys Glu Phe Pro Val Val Leu Asn Ala Phe
145                 150                 155                 160

Val His Gly Asp Val Asp Leu Phe Asn Asn Tyr Pro Glu Leu Gln Glu
                165                 170                 175

Ala Met Val Trp Val Tyr Phe His Ser Lys Ile Pro Glu Phe Asn Lys
            180                 185                 190

Val Glu Cys Trp Gly Pro Leu Lys Asp Pro Ala Pro Pro Ser Thr Gly
        195                 200                 205

Leu Asp Gly Ser Thr Gln Ser Gln Pro Met Trp Glu Leu Gly Leu Leu
    210                 215                 220

Glu Arg Pro Lys Pro Cys Gln Glu Asp Cys Thr Cys Cys Phe Pro Thr
225                 230                 235                 240

Ile Pro Ser Ile Ser Trp Ser Pro Lys Asn Asn Glu Leu Glu Ser Thr
                245                 250                 255
```

STAY GREEN CUCUMBER PLANT

CROSS-REFERENCE TO RELATED APPLICATIONS

This application is the United States national phase of International Application No. PCT/EP2015/066310 filed Jul. 16, 2015, and claims priority to Dutch Patent Application No. 2013260 filed Jul. 25, 2014, the disclosures of which are hereby incorporated in their entirety by reference.

The Sequence Listing associated with this application is filed in electronic format via EFS-Web and is hereby incorporated by reference into the specification in its entirety. The name of the text file containing the Sequence Listing is 1700471_ST25.txt. The size of the text file is 11,462 bytes, and the text file was created on Jan. 17, 2017.

BACKGROUND OF THE INVENTION

The present invention relates to a cucumber plant (*Cucumis sativus*) which provides fruits having an improved shelf life. Further, the present invention relates to seeds, plant tissue, fruits or plants parts of a cucumber plant (*Cucumis sativus*). Further aspect of the present invention relates to a method for providing a cucumber plant (*Cucumis sativus*) which provides fruits with an improved shelf life. According to yet another aspect the present invention relates to nucleic acids and amino acids related to the present improved shelf life trait.

Cucumber plants are already cultivated for at least 3.000 years and several different cultivars have emerged, which are grown and market on the global market. The cucumber fruits are mainly eaten in the unripe green form since the ripe yellow form normally becomes bitter and sour. Accordingly, the cucumber fruits are commonly harvested while still green and are generally used for both the pickling industry and the fresh market, which latter usage has the greatest added value for the farmers. Due to its relatively short shelf life, storage and shipping of fresh cucumber fruits is, however, difficult and expensive. Cooling, which is generally used to extend the shelf life of fresh products, cannot be applied for cucumber fruits as these fruits are not suitable for storage at low temperatures due to chill injury.

It is known to extend the shelf life of cucumber fruits by for example wrapping them in sealing foil or storing them under controlled conditions (>10° C.). However, additional processing steps or specific storage measures thus have to be taken. In addition, in this way the shelf life is extended only in the specific cucumbers that have been wrapped in foil, or have been stored under said specific conditions. Further, although the shelf life is extended by wrapping cucumbers in foil, these wrapped cucumbers turn yellow within a time period of about two weeks.

Given the above, there is a need in the art for cucumber plants providing fruits having an extended shelf life.

SUMMARY OF THE INVENTION

Therefore, it is an object of the invention, amongst other objects, to provide cucumber plants providing fruits having an extend shelf life.

This object, amongst other objects, is met by providing a cucumber plant according to the appended claim 1.

Specifically, this object, amongst other objects, is met by providing a cucumber plant (*Cucumis sativus*) which provides fruits having an improved shelf life, wherein said plant comprises a gene, or stay green gene, providing the improved fruit shelf life, wherein said gene, or stay green gene, encodes a protein comprising the amino acid sequence as shown in SEQ ID NO. 2, or amino acid sequences with more than 90% identity, such as more than 91%, 92% or 93%, preferably more than 94% identity such as more than 95%, more preferably more than 96% identity such as more than 97%, even more preferably more than 98% identity or more than 99% identity; and wherein the expression of said gene, or stay green gene, is reduced as compared to the expression of said gene, or stay green gene, in a cucumber plant not providing fruits having an improved shelf life or the enzymatic activity of said protein is reduced as compared to the enzymatic activity of said protein in a cucumber plant not providing fruits having an improved shelf life.

In the research that led to the present invention, it was surprisingly found that a reduced expression of the present gene or a reduced enzymatic activity of the present protein provided fruits having an extended shelf life for a time period up to five weeks when stored under standard storing conditions for cucumbers.

With improved shelf life, as used in the present context, is meant an improved storability of harvested unripe green cucumbers, which cucumbers stay green for longer periods of time than comparable standard harvested unripe green cucumbers. Preferably, the present cucumbers stay green for a time period up to 4 or 5 weeks.

Plants of the invention can be distinguished from prior art plants by measuring the time period under standard storage conditions that the cucumber fruits stay green. Conventional cucumber fruits turn yellow within 1 or 2 weeks; whereas cucumber fruits according to the present invention turn yellow after a time period of at least 4 or at least 5 weeks.

Further, expression levels in the present plants and the reference plants can be determined using any suitable and generally known Molecular Biology technique such as a quantitative Polymerase Chain Reaction (PCR) or mRNA hybridization.

According to the present invention, an enzymatic activity is reduced in comparison with the activity of the present protein in a cucumber plant which not provides cucumber fruits having an extended shelf life. The term 'not providing cucumber plants having an extended shelf life' indicates a shelf life, determined in an appropriate storability test and appropriate reference plant, such as a parent plant, being less than the shelf life than observed for cucumber fruits of the present invention. Suitable reference plants can, besides parent plants, also be plants generally designated as providing marketable cucumber fruits.

The present protein has a chlorophyll decarboxylase function wherein, amongst other reactions, a carboxyl group is removed and carbon dioxide is released. Accordingly, the present reduced activity can be determined using an assay measuring compounds being either the starting compounds or the resulting compounds of the enzymatic reaction. As a suitable alternative, protein levels, being inherently indicative of a reduced activity, of the present proteins can be determined by, for example, ELISA or protein hybridization both being techniques commonly known to the skilled person.

The present cucumber plants can be obtained by mutagenesis of cucumber plants. For example, mutations, either at the expression level or the protein level, can be introduced in these plants by using mutagenic chemicals such as ethyl methane sulfonate (EMS) or by irradiation of plant material with gamma rays or fast neutrons. The resulting mutations can be directed or random. In the latter case, mutagenized plants carrying mutations in the present gene can be readily identified by using the TILLING (Targeting Induced Local Lesions IN Genomes) method (McCallum et al. (2000) Targeted screening for induced mutations. Nat. Biotechnol. 18, 455-457, and Henikoff et al. (2004) TILLING. Traditional mutagenesis meets functional genomics. Plant Physiol. 135, 630-636). Briefly, this method is based on the PCR amplification of a gene of interest from genomic DNA of a large collection of mutagenized plants in the M2 generation. By DNA sequencing or by scanning for point mutations using a single-strand specific nuclease, such as the CEL-I nuclease (Till et al. (2004) Mismatch cleavage by single-strand specific nucleases. Nucleic Acids Res. 32, 2632-2641) individual plants having a mutation in the present genes are identified.

According to another preferred embodiment of this first aspect of the present invention, the present improved shelf life is provided by one or more mutations in the coding sequence of the present gene resulting in a truncated or non-functional protein. Truncated proteins can be readily determined by analyzing gene transcripts at the mRNA or cDNA level and non-functional proteins can be determined in enzyme assays or using conformation-dependent antibodies. Mutations which can be assayed at the transcript level are, for example, amino acid substitutions, frame-shifts or pre-mature stop codons.

According to yet another preferred embodiment this first aspect of the present invention, the present improved shelf life is provided by one or more mutations in the regulatory regions or non-coding sequences of the present gene. Examples of regulatory regions of the present genes are promotor and terminator regions and examples of non-coding regions are introns and especially splicing influencing motifs therein.

In a further preferred embodiment of the present invention the present mutation results in an amino acid substitution comprising a substitution of leucine, or designated as 1' (Leu), on position 153 of SEQ ID NO. 2. More preferably the leucine on position 153 of SEQ ID NO. 2 is substituted by an phenyl alanine, or 'F' (Phe). Accordingly, in a further preferred embodiment, the present stay green gene encodes a protein comprising an amino acid sequence as shown in SEQ ID NO. 4. This protein comprising the present amino acid sequence as shown in SEQ ID NO. 4 is highly correlated with the improved shelf life trait of the present invention, since an improved shelf life of at least 4 weeks is observed for fruits from a cucumber plant comprising a gene encoding the present protein.

According to yet another preferred embodiment this first aspect of the present invention, the present reduced expression is provided by one or more mutations in the regulatory regions or non-coding sequences of the present genes. Examples of regulatory regions of the present genes are promotor and terminator regions and examples of non-coding regions are introns and especially splicing influencing motifs therein.

According to yet a further preferred embodiment, the present stay green gene is present in homozygous form, thereby providing an improved shelf life of the cucumber fruits. Alternatively, the present stay green gene may be present in heterozygous form, thereby providing an intermediary phenotype.

According to a second aspect, the present invention relates to seeds, plant tissue, fruits or plants parts of a cucumber plant (*Cucumis sativus*) comprising a stay green gene providing an improved fruit shelf life, or alternatively obtainable or derived from the present cucumber plant, wherein the stay green gene encodes an amino acid sequence as shown in SEQ ID NO. 2, or amino acid sequences with more than 90% identity, preferably more than 94% identity, more preferably more than 96% identity, even more preferably more than 98% identity; and wherein the expression of said gene is reduced as compared to the expression of said stay green gene in a cucumber plant not providing fruits having an improved shelf life or the enzymatic activity of said protein is reduced as compared to the enzymatic activity of said protein in a cucumber plant not providing fruits having an improved shelf life.

According to a third aspect the present invention relates to a method for providing a cucumber plant (*Cucumis sativus*) which provides fruits with an improved shelf life, said method comprises the step of introducing in a cucumber plant (*Cucumis sativus*) a stay green gene encoding a protein comprising the amino acid sequence as shown in SEQ ID No. 2, or a gene with more than 90% sequence identity, preferably more than 94% sequence identity, more preferably more than 96% sequence identity with identity SEQ ID No. 2; and wherein the expression of said gene is reduced as compared to the expression of said gene in a cucumber plant not providing fruits having an improved shelf life or the enzymatic activity of said protein is reduced as compared to the enzymatic activity of said protein in a cucumber plant not providing fruits having an improved shelf life.

According to a fourth aspect, the present invention relates to the use of a gene, or the cDNA sequence thereof, encoding a protein comprising the amino acid sequence as shown in SEQ ID No. 2 or a gene encoding a protein with more than 90% sequence identity, preferably more than 94% sequence identity, more preferably more than 96% sequence identity with identity SEQ ID No. 2 for providing cucumber plants (*Cucumis sativus*) which provides fruits with an improved shelf life, or preferably fruits which stay green during storage for a time period of at least 4 or 5 weeks.

According to a fifth aspect, the present invention relates to proteins comprising an amino acid sequence as shown in SEQ ID NO 4.

According to a sixth aspect, the present invention relates to nucleic acids, preferably isolated nucleic acids, comprising SEQ ID NO 3.

According to a seventh aspect, the present invention relates to a gene, or stay green gene, encoding a protein having an amino acid sequence comprising SEQ ID No. 4.

According to an eight aspect the present invention relates to a gene, or stay green gene, comprising a nucleic acid sequence comprising SEQ ID NO. 3.

According to a ninth aspect, the present invention relates to a gene, or stay green gene, as defined above, i.e. wherein said gene, or stay green gene, encodes a protein comprising the amino acid sequence as shown in SEQ ID NO. 2, or amino acid sequences with more than 90% identity, such as more than 91%, 92% or 93%, preferably more than 94% identity such as more than 95%, more preferably more than 96% identity such as more than 97%, even more preferably more than 98% identity or more than 99% identity; wherein said gene comprises a mutation in the coding sequence resulting in one or more amino acid substitutions in comparison with the unmutated gene encoding a protein comprising the amino acid sequence as shown in SEQ ID NO. 2.

BRIEF DESCRIPTION OF THE DRAWINGS

The invention is further elucidated in the illustrative examples below. In the examples, reference is made to figures wherein.

DETAILED DESCRIPTION

Example 1

Two thousand seeds of the Cucumber (*Cucumis sativus*) hybrid Kurios were treated with 0.75% (W/V) Ethyl Methane Sulfonate (EMS) for 16 hours. After rinsing the seeds several times with water, seeds were sown in peet blocks. After appearance of the primary leaf, the apical meristem was removed to induce the development of the lateral meristem. This procedure was repeated to induce outgrowth of the lateral meristem of the first side shoot. Samples were taken from the top of this developing shoot for further molecular analysis i.e. the detection of mutations in candidate genes as described by Van Eijk and Van Tunen in EP 1929039.

A plant derived from the EMS treatment comprising SEQ ID NO. 3 was grown in a greenhouse and cucumber fruits where harvested. The shelf life of the fruits was measured during 4 weeks in a storability test using the following scale: (1) Good colour (green); (2) Acceptable colour (somewhat lighter green); (3) Unacceptable colour (first occurrence of yellowing); (4) Unacceptable colour (yellowing); (5) Unacceptable colour (extreme yellowing). A conventional cucumber fruit derived from a plant not comprising SEQ ID NO. 3 was also measured for 4 weeks in the same storability test.

Figure 1:
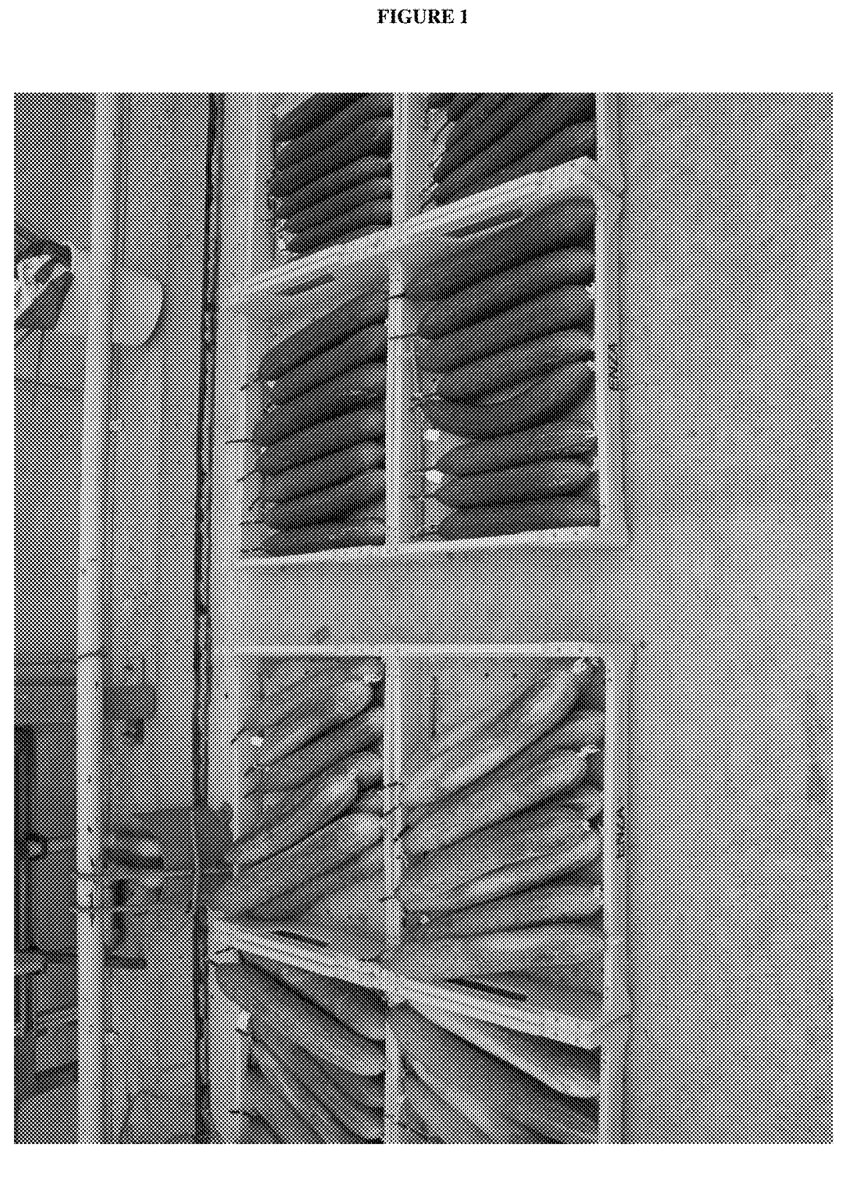
FIG. 1: shows a picture of prior art cucumbers and cucumber according to the present invention 4 weeks after harvest.
Figure 2:
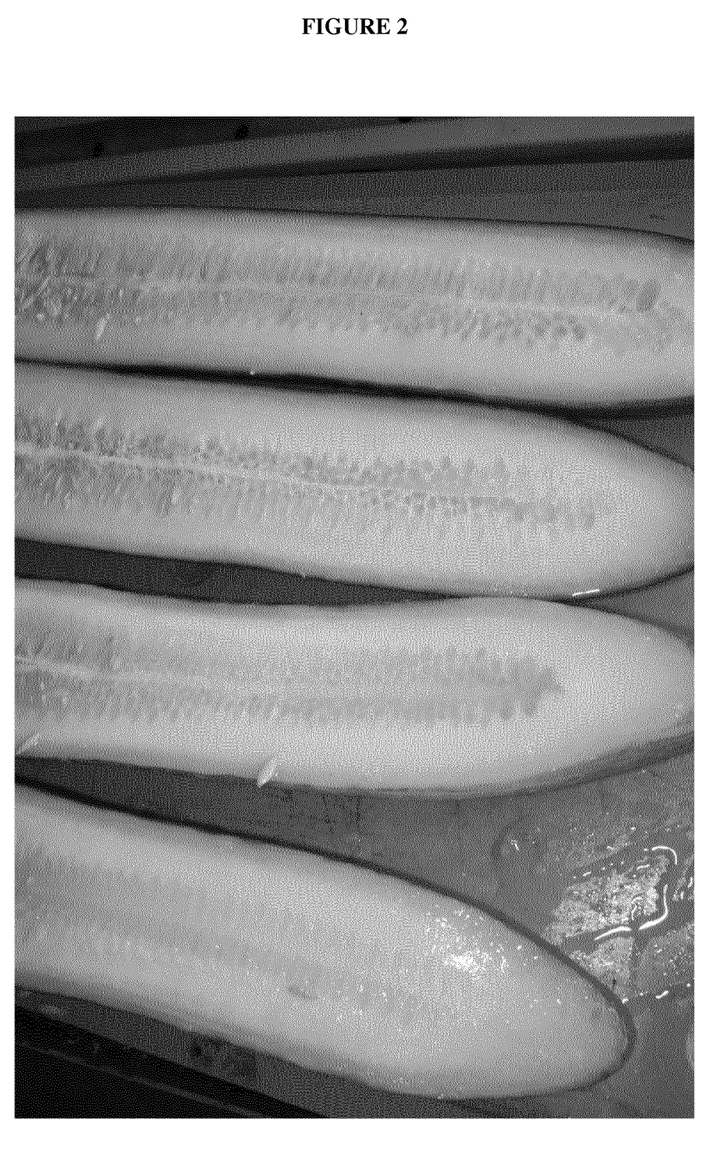
FIG. 2: shows 4 week old prior art cucumbers and cucumbers according to the invention.

The cucumbers according to the invention stayed green during the time period of 4 weeks, with a continuous score (1). The conventional cucumbers show a normal yellowish colour due to chlorophyll degradation during the 4 week test period, reaching score 4 after 4 weeks. FIG. 1 shows a picture with on the left side 4 weeks old conventional cucumbers having a yellowish colour, and on the right side 4 weeks old cucumbers according to the present invention having a full green colour. Further, the presence of SEQ ID NO. 3 also affected the flesh colour of cucumber fruits. 4 week old conventional cucumbers show a normal lighter colour (see FIG. 2, left side) compared to cucumbers harvested from a plant of the present invention, (see FIG. 2, right side).

Example 2

Plants derived from the EMS treatment comprising SEQ ID NO. 3 were grown in the greenhouse together with plants derived from untreated seeds (Wild type/WT) and the reference variety Kurios. From the plants carrying the present stay green gene, both heterozygous (Het) and homozygous (Hom) forms were planted.

Figure 3A:
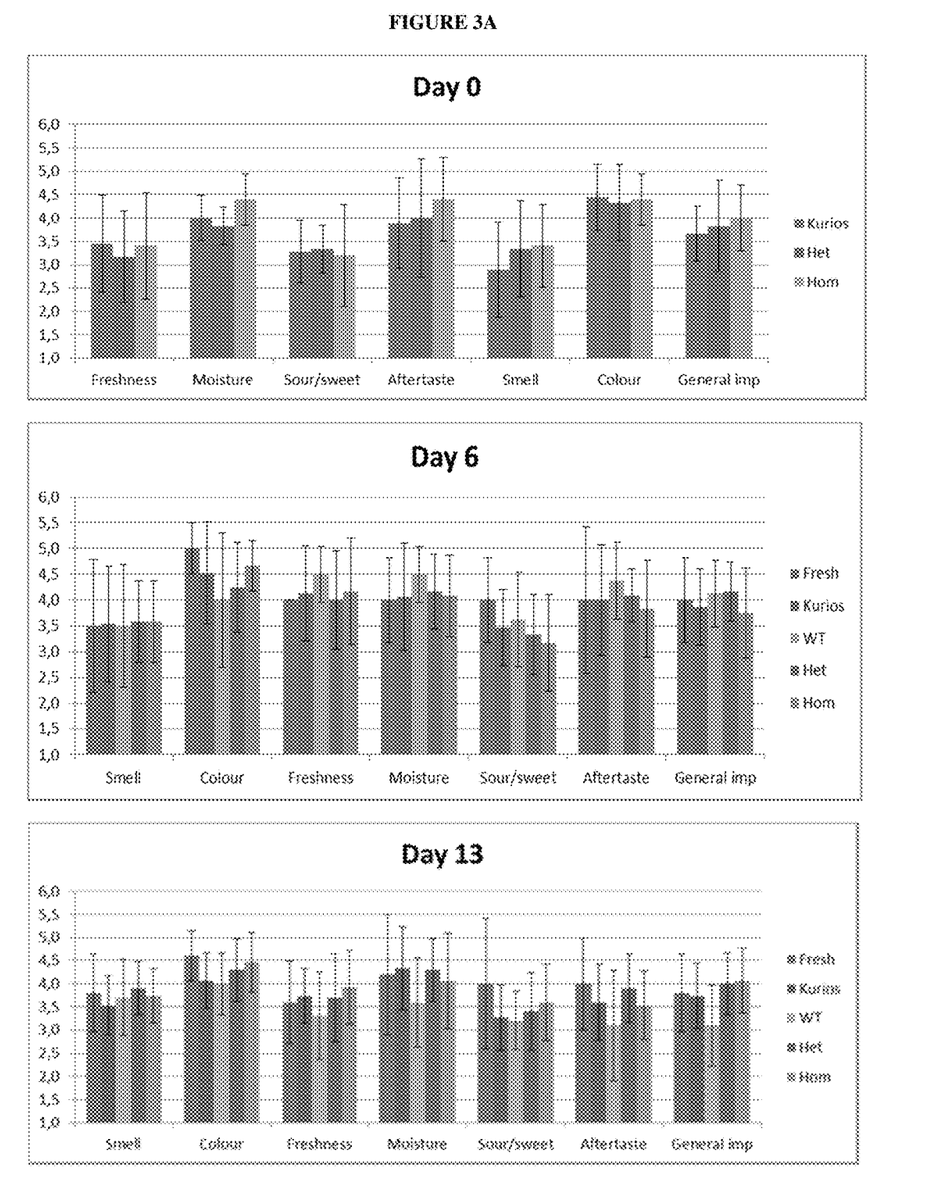
FIG. 3A and 3B: show average scores of the tasting evaluation at day 0, 6, 13 (FIG. 3A) and 20 (FIG. 3B) after harvest of fruits of Kurios, WT, Het and Hom.
Figure 3B:
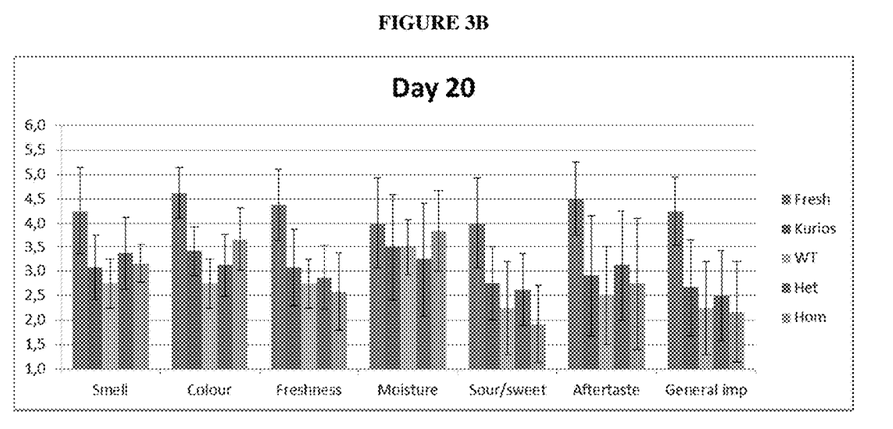

Fruits of the 4 different plant types were harvested on day 0 and stored for 4 weeks in a crate at 17° C. A taste panel has been evaluating the taste of the fruits, giving attention to Freshness, Moisture, Sour/sweet, Aftertaste, Color, Smell, and General impression. Evaluations took place at day 0, day 6, day 13, and day 20 after the fruits were harvested. As a control, at a day of tasting, a fresh fruit of the reference variety Kurios was also harvested and evaluated. The scores, using the scale 1-5, are shown in FIG. 3. It can be concluded that there is little difference between the taste of the 4 different types (Kurios, WT, Het, Hom) at the 4 moments (day 0, day 6, day 13, day 20) of tasting.

Figure 4:
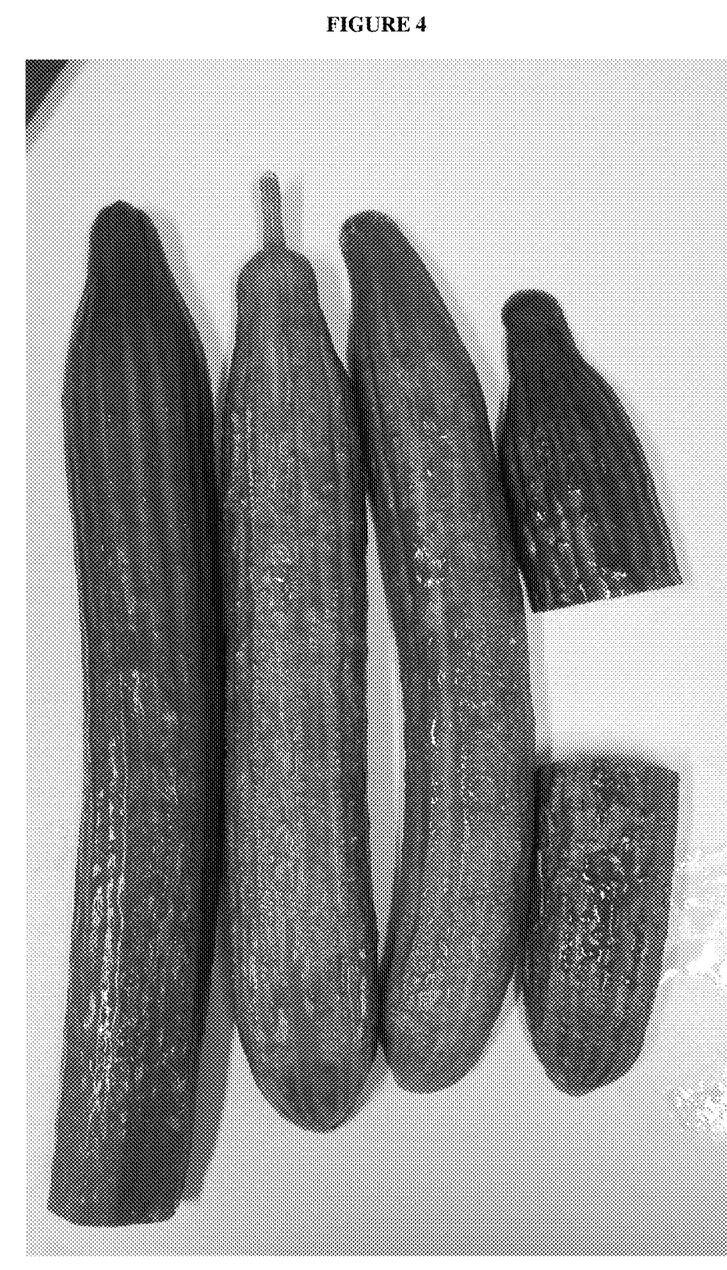
FIG. 4: shows from left to right: Fresh Kurios, 28 days old Kurios, 28 days old heterozygous SGR, 28 days old Homozygous SGR.
Figure 5:
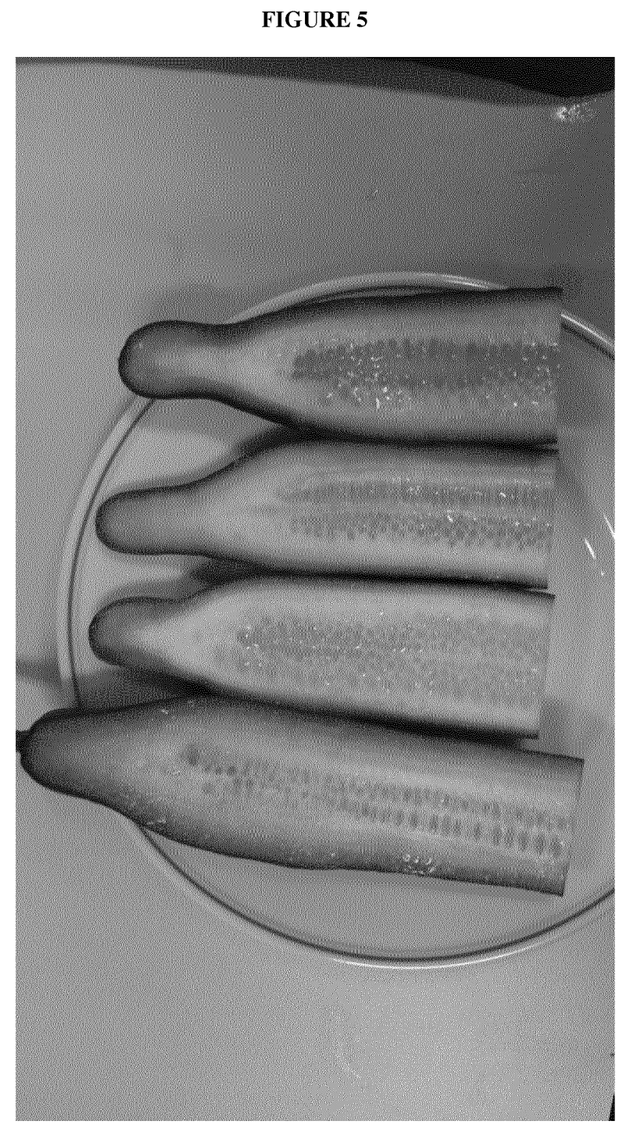
FIG. 5: shows from left to right: Fresh Kurios, 28 days old Kurios (Wild type), 28 days old heterozygous SGR, 28 days old Homozygous SGR.

After 4 weeks of storage, pictures were taken from the fruits. They are shown in FIGS. 4 and 5.

It is clear that the exterior color of the fruit of the homozygous SGR type after 28 days is at least as dark as the fresh picked Kurios fruit. Also the interior color of the fruit of the homozygous SGR type is darker than the fresh picked Kurios fruit, the wild type and the heterozygous type. Also can be concluded from FIGS. 4 and 5, that the other aspects of shelf life (like blisters, soft neck) are not altered by the presence of the stay green gene.

Example 3

Figure 6:
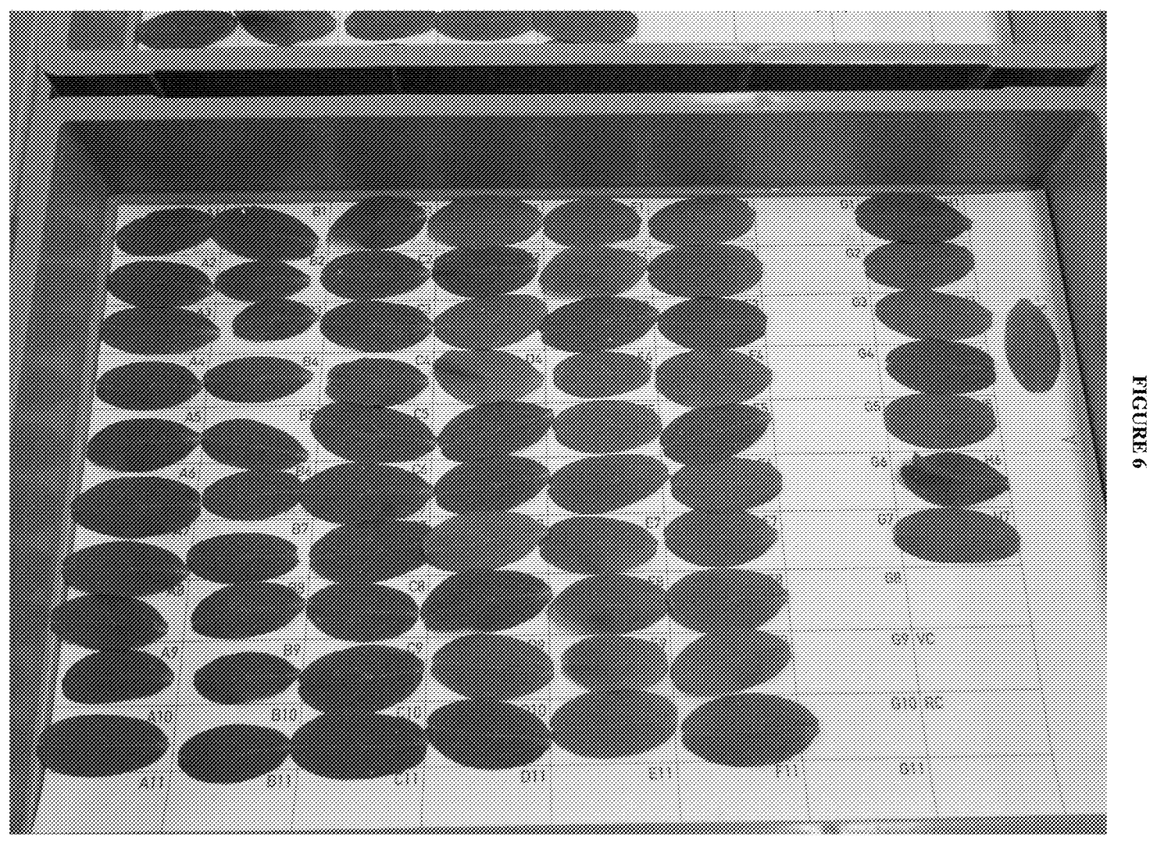
FIG. 6: shows cotyledons stored for 2 weeks.

Seeds of plants with either the present stay green gene in homozygous form or in heterozygous form were grown till the cotyledon stage. The cotyledons were removed from the plantlets and placed in a plastic container covered with a glass plate. It can be considered that there was no air exchange possible between the content of the container and the environment. After 2 weeks of storage, the picture as shown in FIG. 6 was visible.

Cotyledons from plants of seeds that were harvested from the plant with the stay green in the homozygous form were placed on the grid A 1-C11. Cotyledons from plants of seeds that were harvested from the plant with the stay green gene in heterozygous form were placed on the grid D1-F11. In the grid D1-F11 there are 8 cotyledons expressing the stay green gene in a homozygous form (as in the grid A1-C11), and 22 cotyledons lacking this expression. These cotyledons may either lack the stay green gene or have it in a heterozygous form. The ratio 8/22 confirms the expected ratio for a single recessive gene, meaning that the present stay green gene is present in homozygous form.

Example 4

It is common knowledge that leaves of a cucumber plant which are in the lower part of the plant, become old and yellow, and start to disintegrate when they are being covered by upper leaves. The disintegration of the leaf is, amongst others, caused by the inactivity of the chlorophyll. The chlorophyll is giving the green color to the leaf.

Figure 7:
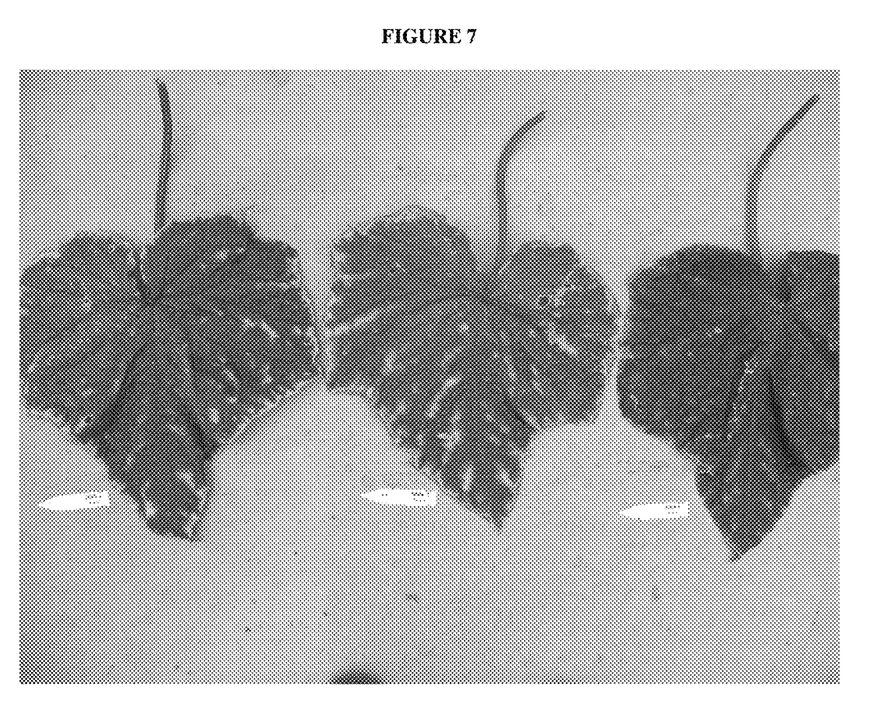
FIG. 7: shows from left to right: mature leaves of the wild type, heterozygous SGR and homozygous SGR

Plants of the wild type (lacking the present stay green gene), plants with the present stay green gene in heterozygous form and plants with the present stay green gene in homozygous form have been planted in the greenhouse. At mature stage of the plants (i.e. after 10 weeks) lower leaves were picked and placed next to each other. The result is shown in FIG. 7.

It is clear the plant with the present stay green gene in homozygous form is able to maintain its chlorophyll for a longer period. Likewise, it is expected that the plant containing this gene in homozygous form is able to be photosynthetic active for a longer period.

The invention claimed is:

1. An isolated cucumber plant having an improved shelf life comprising in its genome a modified gene, the modified gene comprising a mutation in its coding sequence resulting in an amino acid substitution of a leucine at position 153 of SEQ ID NO: 2.

2. The isolated cucumber plant of claim 1, wherein the modified gene encodes a protein having the amino acid sequence of SEQ ID NO: 4.

3. The isolated cucumber plant of claim 1, wherein the modified gene comprises the nucleotide sequence of SEQ ID NO: 3.

4. A seed, fruit, plant part, or propagation material of the isolated cucumber plant of claim 1, wherein the seed, fruit, plant part, or propagation material comprises the modified gene comprising the mutation in its coding sequence resulting in the amino acid substitution of leucine at position 153 of SEQ ID NO: 2.

5. The seed, fruit, plant part, or propagation material of claim 4, wherein the modified gene encodes a protein having the amino acid sequence of SEQ ID NO: 4.

6. The seed, fruit, plant part, or propagation material of claim 4, wherein the modified gene comprises the nucleotide sequence of SEQ ID NO: 3.

* * * * *